United States Patent
Iaccino et al.

(10) Patent No.: US 8,981,169 B2
(45) Date of Patent: *Mar. 17, 2015

(54) METHANE CONVERSION PROCESS

(75) Inventors: Larry L. Iaccino, Seabrook, TX (US);
Robert D. Denton, Bellaire, TX (US);
Garth M. Norman, Houston, TX (US);
James R. Lattner, LaPorte, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 375 days.

This patent is subject to a terminal disclaimer.

(21) Appl. No.: 13/184,954

(22) Filed: Jul. 18, 2011

(65) Prior Publication Data

US 2012/0036889 A1     Feb. 16, 2012

Related U.S. Application Data (60) Provisional application No. 61/372,160, filed on Aug. 10, 2010.

(51) Int. Cl.

| | | |
|---|---|---|
| C07C 15/04 | (2006.01) | |
| C07C 15/00 | (2006.01) | |
| C07C 2/76  | (2006.01) | |
| C10L 3/08  | (2006.01) | |
| F25J 3/02  | (2006.01) | |

(52) U.S. Cl.
CPC ............... *C07C 2/76* (2013.01); *C07C 2529/69* (2013.01); *C10L 3/08* (2013.01); *F25J 3/0209* (2013.01); *F25J 3/0223* (2013.01); *F25J 3/0233* (2013.01); *F25J 3/0252* (2013.01); *F25J 2210/62* (2013.01); *F25J 2215/04* (2013.01); *F25J 2270/904* (2013.01)

USPC ............ 585/413; 585/407; 585/418; 585/419

(58) Field of Classification Search
USPC ......... 585/319, 322, 323, 407, 413, 418, 419, 585/804, 833
See application file for complete search history.

(56) References Cited

U.S. PATENT DOCUMENTS

| | | | | |
|---|---|---|---|---|
| 2,423,328 A | * | 7/1947 | Layng | 208/66 |
| 3,656,312 A | * | 4/1972 | Streich | 62/630 |
| 4,522,793 A | * | 6/1985 | Larson et al. | 423/230 |

(Continued)

FOREIGN PATENT DOCUMENTS

| | | |
|---|---|---|
| CN | 101260330 A | 9/2008 |
| EP | 0 269 297 | 4/1991 |

(Continued)

*Primary Examiner* — Walter D Griffin
*Assistant Examiner* — Jelitza Perez (57) ABSTRACT

A process for converting a gaseous hydrocarbon feed comprising methane to an aromatic hydrocarbon is integrated with liquefied natural gas (LNG) and/or pipeline gas production. The gaseous hydrocarbon feed is supplied to a conversion zone comprising at least one dehydroaromatization catalyst and is contacted with the catalyst under conversion conditions to produce a gaseous effluent stream comprising at least one aromatic compound, unreacted methane and $H_2$. The gaseous effluent stream is then separated into a first product stream comprising said at least one aromatic compound and a second product stream comprising unreacted methane and $H_2$. The second product stream is further separated into a methane-rich stream and a hydrogen-rich stream and at least part of the methane-rich stream is passed to LNG and/or pipeline gas production.

18 Claims, 3 Drawing Sheets

(56) References Cited

U.S. PATENT DOCUMENTS

| | | |
|---|---|---|
| 4,677,235 A | 6/1987 | Mowry |
| 4,727,206 A | 2/1988 | Clayson et al. |
| 5,026,937 A | 6/1991 | Bricker |
| 5,336,825 A | 8/1994 | Choudhary et al. |
| 7,451,618 B2 | 11/2008 | Ansorge et al. |
| 2004/0015025 A1* | 1/2004 | Bellussi et al. ............... 585/319 |
| 2007/0249880 A1* | 10/2007 | Iaccino et al. ................ 585/418 |
| 2007/0260098 A1 | 11/2007 | Iaccino et al. |
| 2007/0276171 A9 | 11/2007 | Iaccino et al. |
| 2008/0021251 A1 | 1/2008 | Iaccino et al. |
| 2008/0047872 A1 | 2/2008 | Iaccino et al. |
| 2009/0205367 A1* | 8/2009 | Price ............................... 62/612 |
| 2010/0256245 A1 | 10/2010 | Iaccino et al. |

FOREIGN PATENT DOCUMENTS

| | | |
|---|---|---|
| JP | 2006-016353 | 1/2006 |
| WO | 2010/104762 | 9/2010 |

* cited by examiner

METHANE CONVERSION PROCESS

PRIORITY CLAIM

This application claims the benefit of U.S. Provisional Application No. 61/372,160, filed Aug. 10, 2010, the entirety of which is incorporated by reference.

FIELD

The present invention relates to a process for the conversion of methane to aromatic hydrocarbons and in particular to integration of such a process with production of liquefied natural gas (LNG) and/or pipeline gas. As used herein, the term "pipeline" gas means any natural gas being used for fuel or as a chemical feedstock where the gas is made available in the vapor phase at the pressure and temperature required for use or transportation.

BACKGROUND

Aromatic hydrocarbons, particularly benzene, toluene, ethylbenzene and xylenes, are important commodity chemicals in the petrochemical industry. Currently, aromatics are mostly frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane, which is the major constituent of natural gas and biogas. World reserves of natural gas are constantly being upgraded and more natural gas is currently being discovered than oil. Because of the problems associated with transportation of large volumes of natural gas, sometimes a significant portion of the natural gas produced along with oil at remote places is flared and wasted. Hence the conversion of alkanes contained in natural gas directly to higher hydrocarbons, such as aromatics, is a particularly desirable method of upgrading natural gas, providing the attendant technical difficulties can be overcome.

A large majority of the existing processes for converting methane to liquid hydrocarbons involve first conversion of the methane to synthesis gas, a blend of $H_2$ and CO. However, the production of synthesis gas is capital and energy intensive; therefore routes that do not require synthesis gas generation are preferred.

A number of other processes have been proposed for directly converting methane to higher hydrocarbons, such as catalytic oxidative coupling of methane to olefins followed by the catalytic conversion of the olefins to liquid hydrocarbons, including aromatic hydrocarbons. See, for example, U.S. Pat. No. 5,336,825. However, oxidative coupling methods suffer from the problem that they involve highly exothermic reactions (and thus are exposed to potentially hazardous methane combustion reactions) and they generate large quantities of environmentally sensitive carbon oxides.

A potentially more attractive route for the direct conversion of methane to higher hydrocarbons is by way of dehydroaromatization, which is a reductive coupling process in which methane is converted to aromatic hydrocarbons, such as benzene, toluene, and naphthalene (commonly referred to collectively as "BTN"), along with hydrogen, using a supported metal catalyst. See, for example, U.S. Pat. No. 5,026,937. However, not only does this process produce large quantities of hydrogen (9 moles of hydrogen for every mole of benzene) but thermodynamic considerations dictate that only a limited amount of the methane feed that can be converted to aromatic products at economically viable operating conditions. Thus, to be successful, any commercial methane dehydroaromatization process must make provision for the separation and use of large quantities of unreacted methane and by-product hydrogen.

For example, recognizing that most natural gas sources also contain large quantities of $CO_2$, U.S. Patent Publication 2007/0260098 discloses a process for converting methane to higher hydrocarbons including aromatic hydrocarbons, in which a methane-containing feed is contacted with a dehydroaromatization catalyst, conveniently molybdenum, tungsten and/or rhenium or a compound thereof of ZSM-5 or an aluminum oxide, under conditions effective to convert the methane to aromatic hydrocarbons and produce a first effluent stream comprising aromatic hydrocarbons and $H_2$, wherein said first effluent stream comprises at least 5 wt % more aromatic rings than said feed. At least part of the $H_2$ from the first effluent stream is then reacted with an oxygen-containing species, such as $CO_2$, to produce a second effluent stream having a reduced $H_2$ content compared with the first effluent stream.

Japanese Unexamined Patent Publication No. 2006016353 discusses methane dehydroaromatization and the effect of sulfur on this reaction system. The catalyst and reaction system of this prior art suffers from very significant catalyst performance deterioration when sulfur is included in the methane containing feed at levels above 10 ppm $H_2S$. For a feed containing 100 ppm $H_2S$, benzene yields over the catalyst life cycle are decreased to about one quarter of the yields with no sulfur present.

Another major use of methane-containing feeds is in the production of pipeline gas and liquefied natural gas (LNG). Pipeline gas is natural gas which has been purified sufficiently to allow its direct use as a fuel or chemical feedstock by both retail and industrial consumers. LNG is natural gas which has been purified and cooled to −260° F. (−162° C.). At this temperature, natural gas condenses into a liquid, which takes up to 600 times less space than in the gaseous form, making it feasible to transport the product over long distances. Both pipeline gas and LNG typically contain at least 85 mol % methane with the balance being higher chain alkanes and so to produce them it is necessary to reduce most impurities in the natural gas feed to very low levels. For example, acid gases, such $H_2S$, mercaptans and carbon dioxide, that are corrosive to the LNG plant and other equipment must be reduced to extremely low levels, for example $H_2S$ levels often have to be below 4 ppm by volume. In addition, water, which could freeze and cause equipment blockage, must be removed, generally to less than 1 ppb in LNG. Similarly, butane and heavier hydrocarbons, which could freeze like water and also have value as chemical feedstocks, are removed typically to levels below 1 to 2% by volume.

To date, some limited proposals have been made to integrate LNG production with conversion of methane to liquid hydrocarbons.

For example, U.S. Pat. No. 7,451,618 discloses a process for liquefying natural gas comprising (a) passing the natural gas at liquefaction pressure through the product side of a main heat exchanger; (b) introducing cooled liquefied refrigerant at refrigerant pressure in the cold side of the main heat exchanger, allowing the cooled refrigerant to evaporate at the refrigerant pressure in the cold side of the main heat exchanger to obtain vaporous refrigerant at refrigerant pressure, and removing vaporous refrigerant from the cold side of the main heat exchanger; (c) removing the liquefied gas at liquefaction pressure from the product side of the main heat exchanger; (d) allowing the cooled liquefied gas to expand to a lower pressure to obtain expanded fluid; (e) supplying the expanded fluid to a separator vessel; (f) withdrawing from the bottom of the separator vessel a liquid product stream; (g) withdrawing from the top of the separator vessel a gaseous stream; (h) introducing the gaseous stream obtained in step (g) as feed and/or fuel in the process for the preparation of liquid hydrocarbons, which process for the preparation of hydrocarbons involves converting a light hydrocarbonaceous feedstock into synthesis gas, followed by catalytic conversion of the synthesis gas into liquid hydrocarbons.

However, while the process of the '618 patent claims efficiencies associated with integration of two processes (natural gas liquefaction and liquid hydrocarbon synthesis), it is still inherently inefficient for at least two reasons, one being the large pressure differential between the liquefaction effluent stream and the preferred operating pressure for the liquid hydrocarbon synthesis, and another being that production of synthesis gas as an intermediate step in the production of liquid hydrocarbons is capital and energy intensive. Accordingly, a more efficient integration of methane conversion technologies with gas liquefaction would be of value.

According to the invention, it has now been found that by integrating methane dehydroaromatization into the feed gas conditioning process of LNG and pipeline gas production, it is possible to significantly reduce the amount of the purification required in the conditioning process. In particular, it is found that many contaminants which are highly problematic in LNG and pipeline gas production, such as water, mercaptans, $H_2S$, and $CO_2$, can be tolerated at higher levels and/or are beneficial and/or are converted to less injurious components in the methane dehydroaromatization process of the present invention. It has been discovered that, unlike the prior-art dehydroaromatization process discussed above, the present dehydroaromatization process can tolerate high levels of sulfur in the range of 100 vppm to 1000 vppm. Since feed gas purification is one of the costliest processes involved in LNG and pipeline gas production, any reduction in the impurity levels required in the feed is potentially of enormous economic benefit. In addition, by integrating methane dehydroaromatization with LNG and pipeline gas production, part of the methane in the natural gas feed is upgraded to higher value aromatic hydrocarbons.

SUMMARY

In one aspect, the invention resides in a process for converting a gaseous hydrocarbon feed comprising methane to an aromatic hydrocarbon and liquefied natural gas (LNG) and/or pipeline gas, the process comprising:

(a) supplying said gaseous hydrocarbon feed to a conversion zone comprising at least one dehydroaromatization catalyst;

(b) contacting said gaseous hydrocarbon feed in said conversion zone with said at least one dehydroaromatization catalyst under conversion conditions to produce a gaseous effluent stream comprising at least one aromatic compound, unreacted methane and $H_2$;

(c) separating said gaseous effluent stream into a first product stream comprising said at least one aromatic compound and a second product stream comprising unreacted methane and $H_2$;

(d) separating said second product stream into a methane-rich stream and a hydrogen-rich stream; and (e) passing at least part of the methane-rich stream to LNG and/or pipeline gas production, wherein said gaseous hydrocarbon feed supplied to said conversion zone in (a) has at least one of the following properties:

(i) a sulfur level of at least 20 ppm by volume;
(ii) a $CO_2$ level of at least 50 ppm by volume; and
(iii) a dew point of at least 203° K.

Conveniently, said gaseous hydrocarbon feed supplied to said conversion zone in (a) has at least one of the following properties:

(i) a sulfur level between about 20 ppm by volume and about 1000 ppm by volume, for example between about 25 ppm by volume and about 200 ppm by volume;

(ii) a $CO_2$ level between about 50 ppm by volume and about 10% by volume, for example greater than about 1% by volume up to about 3% by volume;

(iii) a dew point between about 203° K and an upper water concentration of about 10% by volume, for example, a water content between about 1% by volume and about 5% by volume;

(iv) a nitrogen content between about 0.1% by volume and about 50% by volume, for example between about 1% by volume and about 10% by volume; and (v) an ethane and higher hydrocarbon content up to 20 mol %.

In one embodiment, the process further comprises:

(f) separating a natural gas stream into a first fraction rich in methane and a second fraction rich in ethane;

(g) heating first fraction in a first furnace to produce said gaseous hydrocarbon feed comprising methane;

(h) separately heating said second fraction in a second furnace; and (i) supplying said heated second fraction, together with said gaseous hydrocarbon feed comprising methane, to said conversion zone.

Conveniently, said separation (d) is effected by cryogenic separation to produce a liquid methane-rich stream. In one embodiment, said cryogenic separation is combined with a step of warming and vaporizing a stream of LNG.

Conveniently, the process further includes removing at least one impurity selected from CO, $CO_2$, $H_2S$, and olefins from said second product stream and optionally removing at least one impurity selected from $O_2$ and $N_2$ from said second product stream in said separation (d).

In one embodiment, at least part of said hydrogen-rich stream is employed to regenerate said at least one dehydroaromatization catalyst. In another embodiment, at least part of said hydrogen-rich stream is reacted with $CO_2$ to produce methanol and at least part of said methanol is reacted with benzene produced in said contacting (a) to produce xylene.

Conveniently, said gaseous effluent stream exiting the conversion zone is at a pressure of least 40 psia (275 kPa), such as at least 100 psia (690 kPa).

Conveniently, the sulfur level in the gaseous hydrocarbon feed to a conversion zone comprising at least one dehydroaromatization catalyst may be controlled in order to minimize coking of methane or heavier hydrocarbons in the feed preheat furnace or furnaces for the conversion zone.

DETAILED DESCRIPTION OF THE EMBODIMENTS

Described herein is a process for integrating the dehydroaromatization of methane with at least the gas conditioning steps of the production of pipeline gas and/or liquefied natural gas (LNG). This integration not only allows the gas conditioning steps to be significantly simplified but also permits some of the methane in the natural gas feed to be upgraded to higher value aromatic products. Additional back-end clean up of the unreacted methane may be necessary before its use as pipeline gas and/or LNG. However, overall the capital and operating costs of natural gas purification are significantly reduced in the integrated process as compared with a conventional stand-alone pipeline gas or LNG production plant. Additional efficiencies can be realized by introducing further integration of the processes, for example using the heat required to regasify an LNG stream to assist in the cryogenic separation of the unreacted methane from the hydrogen by-product of the dehydroaromatization process.

Natural Gas Conditioning

Figure 1:
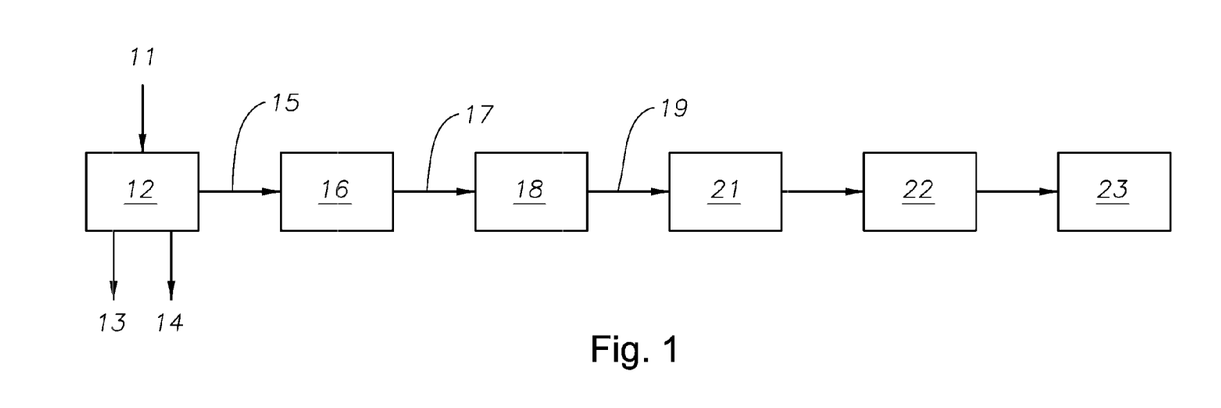
FIG. 1 is a simplified flow diagram of a conventional process for the production of liquefied natural gas (LNG).

Referring to FIG. 1, in a conventional LNG production process, natural gas from one or a plurality of wells is collected and fed by supply line 11 to an inlet facility 12 where free water and entrained heavy ($C_5$+) hydrocarbons are removed via lines 13 and 14 respectively. The raw gas is then fed by pipeline 15 to a gas processing plant, where the gas is normally received by one or more acid gas removal units 16. The units 16, which typically contain solvents, but may also use low temperature separation or membranes or a combination of these processes, serve to remove acid gases, particularly carbon dioxide, hydrogen sulfide and some mercaptans, from the gas. Generally, the gas leaving the units 16 in a conventional LNG production process contains less than 4 ppm by volume $H_2S$, less than 20 ppm by volume total sulfur and less than 50 ppm by volume carbon dioxide. The hydrogen sulfide and mercaptans removed from the gas by the units 16 are generally recovered and converted to elemental sulfur, whereas the carbon dioxide is vented to atmosphere or recompressed for transportation or reinjection into the earth.

After passage through the acid gas removal units 16, the gas is fed by line 17 to one or more dehydration units 18, where water is removed from the gas to reduce its dew point. In the case of a conventional LNG production process, the dew point is normally reduced to less than −173° C. (100° K), whereas with pipline gas a dew point reduction to less than −30° C. (243° K) is normally acceptable. Water removal typically involves at least one of regenerable absorption using triethylene glycol, refrigeration to knock out free water and then if necessary drying with a molecular sieve.

Following water removal, the gas is often fed by line 19 to a natural gas liquid (NGL) recovery unit 21 where $C_2$ to $C_4$ hydrocarbons are removed from the gas. The NGL recovery is generally effected by another low temperature distillation process involving expansion of the gas through a turbo-expander followed by distillation in a demethanizing fractionation column. The NGL liquids are then subjected to further fractionation to separate the liquids into separate ethane, propane and butane streams. Generally, the gas leaving the unit 21 in a conventional LNG production process contains less than 10 mol % ethane, and often much less depending upon the level of ethane recovery.

After water and optional NGL removal, and depending on the $N_2$ specification of both the natural gas feed and the final LNG and/or sales gas, the gas may be fed to a nitrogen removal stage (not shown), which is generally a cryogenic process using low temperature distillation.

Following the gas processing steps, the gas is fed to a compressor 22 where the gas is recompressed and then the recompressed gas is fed to a cryogenic unit 23 to produce the desired LNG. This recompression step is often not required if NGL recovery and/or nitrogen rejection is not employed in conditioning the inlet gas stream.

Figure 2:
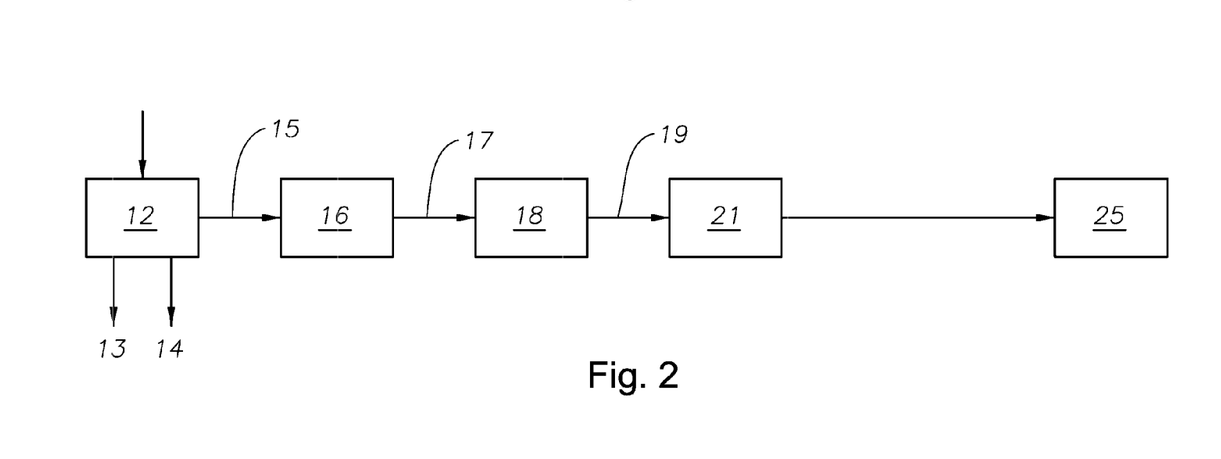
FIG. 2 is a simplified flow diagram of the gas conditioning stage of an integrated process for methane dehydroaromatization and LNG production according to one example of the invention.

Referring now to FIG. 2, in the integrated methane dehydroaromatization/LNG production process shows a similar gas conditioning process is employed to that illustrated in FIG. 1 and so like numerals are used to indicate the same components in both drawings. Thus in the integrated process, natural gas is collected and fed by supply line 11 to an inlet facility 12 where free water and entrained heavy ($C_5$+) hydrocarbons are removed via lines 13 and 14 respectively. The raw gas is then fed by pipeline 15 to one or more acid gas removal units 16, where acid gases, such as carbon dioxide, hydrogen sulfide and some mercaptans, are removed from the gas. In this case, however, the acid gas removal units 16 are only required to reduce the sulfur level in the gas to at least 20 ppm by volume, typically to between about 25 ppm by volume and about 1000 ppm by volume, such as between about 25 ppm by volume and about 200 ppm by volume. Thus, all sulfur compounds, including mercaptans, in the gas are converted to $H_2S$ in the subsequent dehydroaromatization process by reactions such as the following:

$$CH_3SH+H_2 \rightarrow H_2S+CH_4$$

Moreover, contrary to indications in the prior art, the dehydroaromatization catalyst is found to be generally $H_2S$ tolerant. In addition, removal of $H_2S$ from the dehydroaromatization reaction effluent is generally simpler and cheaper than removal of mercaptans from the natural gas stream.

Similarly, the level of carbon dioxide remaining in the feed after passage through the acid gas removal units 16 in the integrated process can be significantly higher than is permissible in the stand-alone LNG process since carbon dioxide acts to reduce coking of the dehydroaromatization catalyst, although also reduces aromatics yield. Generally, the carbon dioxide content of the feed gas after acid gas reduction in the integrated process is greater than 50 ppm by volume, such as from greater than 50 ppm by volume up to about 10% by volume, for example from about 0.1% by volume to about 10% by volume, such as from about 1% by volume to about 3% by volume. In addition, and as will be discussed in more detail below, at least part of the carbon dioxide removed from the natural gas in the integrated process can be used to alkylate the benzene product of the dehydroaromatization process to produce xylenes.

After passage through the acid gas removal units 16, the natural gas feed in the integrated process is fed by line 17 to one or more dehydration units 18, where again water is removed from the gas to reduce its dew point. However, in this case, the dew point is only reduced to at least −70° C. (203° K). The actual dew point will be set by the temperature required to recover the NGLs. If no NGLs need to be recovered or only limited C3+NGLs are recovered, then the dew point can be much higher.

After water removal, the gas is fed by line 19 to a natural gas liquid (NGL) recovery unit 21 where $C_2$ to $C_4$ hydrocarbons are removed from the gas. In the integrated process, the need to remove these components of the gas feed is largely obviated since $C_2$ to $C_4$ hydrocarbons will react to produce aromatics in the dehydroaromatization reaction. However, propane and butane are high value chemical feedstocks and so will generally be recovered as much as economically viable from natural gas feed. Ethane generally has less value external to the dehydroaromatization process and its removal varies from near 100% where there is a ready market to near zero, where only $C_3$+ removal is desired.

In the present integrated process, there is no requirement for the removal of nitrogen from the natural gas feed since nitrogen is inert to the dehydroaromatization process and facilitates separation of the by-product hydrogen from the unreacted methane in the dehydroaromatization process effluent. Thus, the purified natural gas feed to the dehydroaromatization process can contain up to 50 mol % nitrogen, more typically from about 1% by volume to about 10% by volume nitrogen. In fact, where a dehydroaromatization unit is to be integrated with an existing LNG plant containing a nitrogen recovery unit, it is preferential to effect the nitrogen rejection along with the hydrogen and methane separation after the effluent has been dried and recompressed.

In some cases, since ethane has a higher tendency to coke than methane during pre-heating of the feed to the temperature required for the dehydroaromatization process (typically 800 to 1200° C.), it may be desirable to separate ethane from the natural gas feed in the NGL recovery unit 21 and pre-heat the ethane and the remainder of feed in separate furnaces or other devices for preheating the feed before supplying the pre-heated feeds to the dehydroaromatization reactor. One option for reducing coke formation during pre-heating of the feed to the dehydroaromatization reactor is to inject $H_2S$ into the stream to reduce carburization of the metal surfaces of the preheat furnaces. This is not possible in the prior art dehydroaromatization processes due to deleterious effects of sulfur on the catalyst of the prior art processes. For the present invention, sulfur content of the feed gas may be controlled to control coke formation in preheat furnaces. One option for doing this is to control upstream feed sulfur removal processes, for example amine treating or mercaptan removal to allow more $H_2S$ and other sulfur compounds to remain in the feed gas and thereby control the amount of coke formation. This would have added benefit in reducing the cost of gas treating. Optionally $H_2S$ and/or other sulfur compounds could be injected into the feed to the preheat furnaces of the dehydroaromatization process. $H_2S$ content in the feed gas to a preheat furnace could be in the range of 25 ppm by volume up to 1-2% as long as the total combined feed sulfur level to the dehydroaromatization process is no greater than 1000 ppm by volume. The latter (1-2%) would result if most of the feed sulfur were included in the optional ethane preheat furnace.

Figure 3:
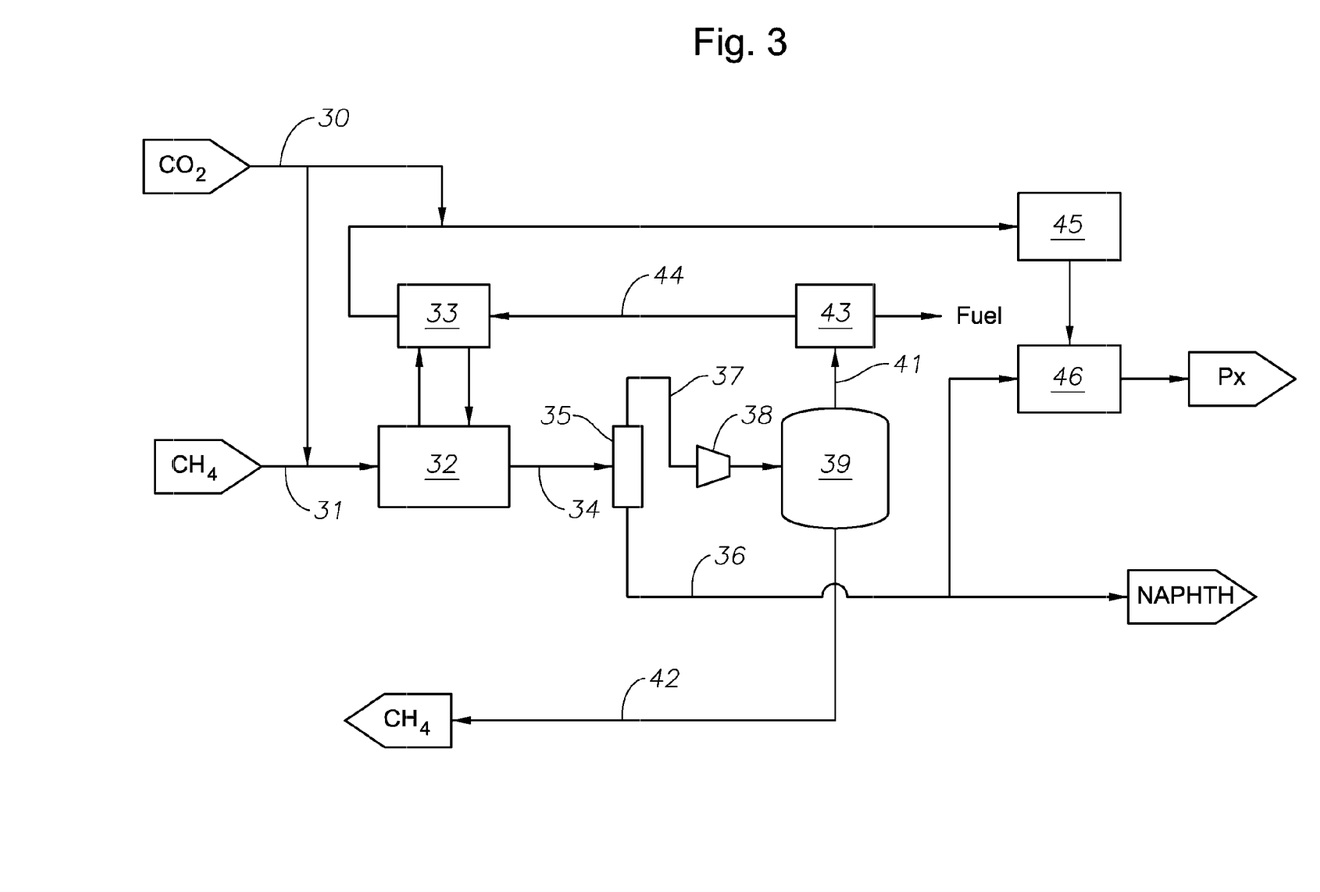
FIG. 3 is a simplified flow diagram of the methane dehydroaromatization stage of the integrated process according to said one example of the invention.

After removal of some or all of the heavier hydrocarbons, the methane-rich gas feed is fed directly to the dehydroaromatization process, which is indicated generally at 25 in FIG. 2 and illustrated in more detail in FIG. 3. Thus in the integrated process the effluent from the NGL recovery unit 21 does not require recompression in the compressor 22 as required for LNG production.

Methane Aromatization

Referring now to FIG. 3, in the dehydroaromatization stage of the integrated process shown, the methane-rich feed from the natural gas conditioning process shown in FIG. 3 is fed by line 31 to a pre-heater (not shown) and then to a dehydroaromatization reactor 32. In addition, carbon dioxide is generally fed to the reactor 32 via line 30, in which case the carbon dioxide can be introduced from a separate supply and/or can be recovered from the acid gas removal step of the gas conditioning process. In one embodiment, the feed to the dehydroaromatization reactor 32 comprises about 90 to about 99.9 mol %, such as about 97 to about 99 mol % methane and about 0.1 to about 10 mol %, such as about 1 to about 3 mol % $CO_2$. In another embodiment, the feed to the dehydroaromatization reactor 32 contains carbon monoxide and comprises about 80 to about 99.9 mol %, such as about 94 to about 99 mol % methane and about 0.1 to about 20 mol %, such as about 1 to about 6 mol % CO. In a further embodiment, the feed to the dehydroaromatization reactor 32 contains steam and comprises about 90 to about 99.9 mol %, such as about 97 to about 99 mol % methane and about 0.1 to about 10 mol %, such as about 1 to about 5 mol % steam. In yet a further embodiment, the feed to the dehydroaromatization reactor 32 contains $H_2$ and comprises about 80 to about 99.9 mol %, such as about 95 to about 99 mol % methane and about 0.1 to about 20 mol %, such as about 1 to about 5 mol % $H_2$.

The feed to the dehydroaromatization reactor 32 can also contain higher hydrocarbons than methane, including aromatic hydrocarbons. Such higher hydrocarbons can be recycled from a $H_2$ rejection step, added as separate co-feeds or can be present in or recovered from the natural gas feed, such as, for example, when ethane is present in the natural gas feed. Higher hydrocarbons recycled from a $H_2$ rejection step typically include one-ring aromatics and/or paraffins and olefins having predominately 6 or less, such as 5 or less, for example 4 or less, typically 3 or less carbon atoms. Generally, the feed to the dehydroaromatization reactor contains less than 5 wt %, such as less than 3 wt %, of $C_3$+ hydrocarbons.

The dehydroaromatization reactor 32 contains a catalyst effective to convert methane to higher hydrocarbons, including benzene and naphthalene, according to the following principal net reactions:

$$2CH_4 \leftrightarrow C_2H_4 + 2H_2$$

$$6CH_4 \leftrightarrow C_6H_6 + 9H_2$$

$$10CH_4 \leftrightarrow C_{10}H_8 + 16H_2$$

Carbon dioxide that may be present in the feed improves catalyst activity and stability by facilitating reactions such as:

$$CO_2 + coke \rightarrow 2CO$$

but negatively impacts equilibrium by allowing competing net reactions, such as:

$$CO_2 + CH_4 \leftrightarrow 2CO + 2H_2.$$

Other oxygenates in the feed, such as water remaining after the natural gas conditioning process shown in FIG. 2, are similarly converted to carbon monoxide. In this respect, it is to be appreciated that the presence of carbon monoxide in the dehydroaromatization reaction effluent is not a problem since carbon monoxide will not freeze in any subsequent cryogenic separation of the hydrogen and methane in the reaction effluent. In fact, the carbon monoxide behaves very much like nitrogen ($N_2$) in the cryogenic distillation and would exit with the $N_2$ and $H_2$ stream as either fuel gas or regeneration gas. The LNG would contain a very low content of carbon monoxide. Moreover, as discussed below, carbon monoxide can be recovered and used in downstream reactions, such as synthesis of methanol and Fischer-Tropsch liquids.

The dehydroaromatization catalyst generally includes a metal component, particularly a transition metal or compound thereof, on an inorganic support. In many cases the support may modify the catalytic behavior of the metal component or may even have some catalytic activity of its own. Preferably, the metal component is present in an amount between 0.1% and 20%, or between 1% and 10%, by weight of the total catalyst.

Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, silicon, germanium, indium, tin, lead, bismuth, and transuranium metals. Such metal components may be present in elemental form or as metal compounds, such as oxides, carbides, nitrides, sulfides and/or phosphides, and may be employed alone or in combination. Platinum and osmium can also be used as one of the metal component but, in general, are not preferred.

The inorganic support may be either amorphous or crystalline and in particular may be an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous crystalline material or a mesoporous material. As used herein the term "microporous" refers to pores having a diameter of less than 2 nanometers, whereas the term "mesoporous" refers to pores having a diameter of from 2 to 50 nanometers.

Suitable microporous crystalline materials include silicates, aluminosilicates, titanosilicates, aluminophosphates, metallophosphates, silicoaluminophosphates, or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49, and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y, and dealuminized Y), LTL (e.g., zeolite L), IWW (e.g., ITQ-22), VFI (e.g., VPI-5), AEL (e.g., SAPO-11), AFI (e.g., ALPO-5), and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34, and SAPO-35. Suitable mesoporous materials include MCM-41, MCM-48, MCM-50, and SBA-15.

Examples of preferred catalysts include molybdenum, tungsten, zinc, rhenium, and compounds and combinations thereof on ZSM-5, silica, or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion, and physical mixing. In addition, the inorganic support can be modified by known methods, such as, for example, steaming, acid washing, caustic washing, and/or treatment with silicon-containing compounds, phosphorus-containing compounds, and/or elements or compounds of Groups 1, 2, 3, and 13 of the Periodic Table of the Elements. Such modifications can be used to alter the surface activity of the support and hinder or enhance access to any internal pore structure of the support.

The catalyst may also include a binder to provide the catalyst particles with the requisite size, density and hardness for use in the dehydroaromatization process. Suitable binders include refractory inorganic oxides such as alumina, silica, amorphous silica-alumina, zirconia, titanium oxide, and boron oxide. The catalyst may also contain fillers to adjust physical properties such as density and heat capacity. Preferred fillers are low surface area, low activity materials with SiC being preferred.

Prior to use in the dehydroaromatization reaction, the catalyst is conveniently subjected to a carburization step to at least partly convert the metal component on the catalyst to its catalytically active elemental or carbide form. This carburization is preferred when the catalyst is to be utilized to process a feed containing significant amounts of sulfur, for example greater than 1 ppm sulfur, greater than 10 ppm sulfur, or even greater than 100 ppm sulfur. The carburization step may be effected by contacting the catalyst with $H_2$, and CO, $CO_2$, and/or a hydrocarbon, such as methane, ethane, or propane, at a temperature from about 400° C. to about 1100° C., such as from about 500° C. to about 900° C., and a pressure from about 10 to about 100 psia (69 to 690 kPa), such as from about 15 to about 60 psia (103 to 414 kPa) for a time from about 0.1 to about 100 minutes, for example from about 1 to about 20 minutes.

The dehydroaromatization reactor 32 comprises one or more fixed bed, moving bed or fluidized bed reaction zones. Generally, the feedstock is contacted in the or each reaction zone with a moving bed of dehydrocyclization catalyst, wherein the feedstock flows countercurrent to the direction of movement of the dehydrocyclization catalyst. In one embodiment, the or each reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed. In an alternative embodiment, the dehydrocyclization reaction is conducted in a plurality of series-connected fluidized bed reactors in which particulate catalyst is cascaded in one direction from one reactor to the next adjacent reactor in the series, while the feed is passed through and between the reactors in the opposite direction.

Examples of suitable reactor designs for the reactor 32 are disclosed in U.S. Published Patent Application Nos. 2007/0129587, 2007/0249879, 2007/0249880, 2007/0276171 and 2007/0293709, the entire disclosures of which are incorporated herein by reference.

The dehydroaromatization reaction is endothermic and the catalytic particulate material enters the reactor 32 at a first, high temperature, typically about 800° C. to about 1200° C., such as about 900° C. to about 1100° C., and exits the reaction system at a second lower temperature, typically about 500° C. to about 800° C., such as about 600° C. to about 700° C. The total temperature difference of the catalytic particulate material across the reaction zones is at least 100° C. Other conditions used in the dehydroaromatization reaction generally include a pressure of about 1 kPa to about 1000 kPa, such as about 10 to about 500 kPa, for example about 50 kPa to about 200 kPa and a weight hourly space velocity of about 0.01 to about 1000 $hr^{-1}$, such as about 0.1 to about 500 $hr^{-1}$, for example about 1 to about 20 $hr^{-1}$. Conveniently, the dehydroaromatization step is conducted in the absence of $O_2$.

The dehydroaromatization reaction tends to deposit coke on the catalyst and hence, to maintain the activity of the catalyst, at least part of the catalyst is continuously or intermittently regenerated. This is typically achieved by withdrawing a portion of the catalyst from the reactor 32, either on an intermittent, or a continuous basis, and then transferring the catalyst portion to a separate regeneration zone 33. In the regeneration zone 33, the coked dehydroaromatization catalyst is contacted with a regeneration gas, conveniently hydrogen generated as a by-product of the dehydroaromatization reaction, under conditions effective to remove at least a portion of the carbonaceous material on the catalyst. The regeneration zone 33 may be a reactor operated as a fluidized bed, an ebulating bed, a settling bed, a riser reactor or a combination thereof. In practice, the regeneration zone 33 may include a plurality of reactors, such as a plurality of riser reactors connected in parallel or a plurality of reactors connected in series such as a riser reactor followed by a settling bed. After regeneration the catalyst is returned to the dehydroaromatization reactor 32.

The major components of the effluent from the dehydroaromatization reactor 32 are hydrogen, benzene, toluene, naphthalene, carbon monoxide, ethylene, and unreacted methane. Typically, the effluent contains at least 5 wt %, such as at least 10 wt %, for example at least 20 wt %, conveniently at least 30 wt %, more aromatic rings than the feed. The effluent from the reactor 32 is typically at a pressure of least 40 psia (275 kPa), such as at least 100 psia (690 kPa), and is fed via line 34 to a compressor (not shown) and then to a gas/liquid separator 35, where the aromatics, principally benzene, toluene and naphthalene (BTN), are condensed from the gaseous product and recovered via line 36.

The crude gaseous product remaining separation of the aromatic liquids is removed from the separator 35 via line 37 and is initially passed through one or more purification stages (not shown) to remove at least one impurity selected from CO, $CO_2$, $H_2S$, and olefins. One suitable purification stage involves treatment with an amine, such as methyldiethanolamine (MDEA), to remove acid gases, especially $H_2S$. In one embodiment, further integration with the gas processing stage can be realized by employing a single acid gas removal unit for initial treatment of the natural gas and for treatment of the gaseous effluent from the dehydroaromatization reactor 32. In particular, fresh or freshly regenerated amine can be used to remove low levels of $H_2S$ in the dehydroaromatization effluent and the resultant amine (containing some sulfur) can then be used for bulk $CO_2$ and $H_2S$ removal from the natural gas feed along with the amount of freshly generated amine required to effect the desired level of purification. In another embodiment the amine regenerator can be configured to have lean and semi-lean amine streams with the lean stream being used to treat the dehydroaromatization effluent and the semi-lean steam, optionally combined with the resultant amine from treating the dehydroaromatization effluent, being used for bulk $CO_2$ and $H_2S$ removal from the natural gas feed. Another suitable purification stage involves hydrogenation to remove olefins either by conversion to the equivalent paraffin or to methane. Olefins can also be removed by cryogenic separation.

After purification, the gaseous product stream is composed mainly of methane, hydrogen, nitrogen and carbon monoxide and in some cases can be used directly as a fuel gas, possibly after removal of some of the carbon monoxide. Generally, however, the purified gaseous product stream is fed to a compressor 38 and then to a cryogenic fractionation unit 39 for separation of the methane. The cryogenic fractionation unit 39 cools the gaseous product, optionally by being used to regasify an LNG stream, to a temperature of below −180° C. so as to separate the product into a methane-depleted, $H_2$-enriched stream 41 and an $H_2$-depleted, methane-enriched stream 42. The cryogenic separation can also be used to remove $O_2$, CO and $N_2$ from the gaseous product. In some cases, part of the methane/hydrogen/carbon monoxide stream can by-pass the cryogenic fractionation unit 39 and be converted to synthesis gas for use in the production of methanol and/or Fischer-Tropsch liquids.

The $H_2$-depleted, methane-enriched stream 42 separated in the cryogenic fractionation unit 39 can be vaporized completely and used directly as pipeline gas or flashed and further cooled to produce liquefied natural gas (LNG).

The methane-depleted, $H_2$-enriched stream 41 is initially passed to a purification device 43, e.g., an adsorption device, where impurities, particularly any remaining traces of $H_2S$, are removed. The resultant purified $H_2$-rich stream 44 is then either fed to the regeneration zone 33 or is mixed with further carbon dioxide from the line 30 and passed to a methanol synthesis unit 45. In the methanol synthesis unit 45, methanol is produced from the carbon dioxide and hydrogen according to the well-known reaction:

$$CO_2 + 3H_2 \leftrightarrow CH_3OH + H_2O$$

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In some embodiments, the methanol synthesis catalyst is selected from the group consisting of copper oxides, zinc oxides and aluminum oxides. More preferably, the catalyst contains oxides of copper and zinc.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa-a to about 12,500 kPa-a, such as from about 2,000 kPa-a to about 10,000 kPa-a, for example 2,500 kPa-a to about 7,500 kPa-a. Gas hourly space velocities vary depending upon the type of process that is used, but generally the gas hourly space velocity of flow of gas through the catalyst bed is in the range of from about 50 $hr^{-1}$ to about 50,000 $hr^{-1}$, such as from about 250 $hr^{-1}$ to about 25,000 $hr^{-1}$, more preferably from about 500 $hr^{-1}$ to about 10,000 $hr^{-1}$. This exothermic reaction may be carried out in either fixed or fluidizing beds, including multiple catalyst beds with heat removal between beds. In addition, the lead bed(s) may be operated at higher temperatures to maximize kinetic rates and the tail bed(s) may be operated at lower temperatures to maximize thermodynamic conversion.

The methanol produced in the methanol synthesis unit 45 is then fed to an alkylation reactor 46 where the methanol is reacted with part of all of the benzene recovered from the dehydroaromatization process via line 36 to produce xylenes, particularly para-xylene. Suitable acid catalysts for this alkylation step include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e., those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56). The alkylation can be conducted in the liquid or vapor phase. Suitable conditions for carrying out the vapor phase alkylation of benzene with methanol include a temperature of from about 650 to 900° F. (343 to 482° C.), a pressure of about atmospheric to about 3000 psig (100 to 20,800 kPa-a), a WHSV based on methanol of from about 0.5 to about 2.0 hr$^{-1}$ and a mole ratio of benzene to methanol of from 1:1 to 30:1. Liquid phase alkylation of benzene with methanol may be carried out at a temperature between 300 and 650° F. (150 to 340° C.), a pressure up to about 3000 psig (20,800 kPa-a), a WHSV based on methanol of from about 0.1 to about 20 hr$^{-1}$ and a mole ratio of benzene to methanol of from 1:1 to 30:1.

Product Differentiation

It will be appreciated that aromatic hydrocarbons, like all hydrocarbons, inherently contain deuterium and $^{13}C$ in amounts that can vary according to the source of the carbon and hydrogen atoms in the molecule. In particular, studies of isotope distributions have shown that the amounts of deuterium and $^{13}C$ in naturally-occurring geologic methane are significantly different from the amounts of deuterium and $^{13}C$ in naphtha and that the amount of $^{13}C$ in naturally-occurring geologic $CO_2$ is significantly different from the amounts of $^{13}C$ in naturally-occurring geologic methane and in naphtha. Thus, analysis of the distribution of deuterium and $^{13}C$, can be used to differentiate between aromatic hydrocarbons produced using the present integrated dehydroaromatization/LNG process and aromatic hydrocarbons produced from naphtha.

Thus, for example, if the measure of isotope abundance for deuterium in a benzene or xylene sample is defined as:

$$\delta(\text{deuterium}) = (R'_{sample}/R'_{standard} - 1) \times 1000$$

where $R'_{sample}$ the ratio of deuterium to hydrogen in the benzene or xylene; and $R'_{standard}$ is the ratio of the natural abundance of deuterium to the natural abundance of hydrogen (which is equal to 0.00015/0.99985); and the measure of isotope abundance for $^{13}C$ in the sample is defined as:

$$\delta(^{13}C) = (R''_{sample}/R''_{standard} - 1) \times 1000$$

where $R''_{sample}$ is the ratio of $^{13}C$ to $^{12}C$ in the benzene or xylene; and $R''_{standard}$ is the ratio of the natural abundance of $^{13}C$ to the natural abundance of $^{12}C$ (which is equal to 0.01109/0.98891), then the following apply:

(a) benzene produced according to the present process comprises deuterium and $^{13}C$ in amounts such that δ(deuterium) for the benzene is less than −250, preferably greater than −450 and less than −250, and $\delta(^{13}C)$ for the benzene is less than −24, preferably greater than −59 and less than −24; and (b) xylene produced according to the present process comprises deuterium and $^{13}C$ in amounts such that the δ(deuterium) value is less than −250, preferably greater than −450 and less than −250, or the $\delta(^{13}C)$ value is less than −24, preferably greater than −60 and less than −24.

The isotopic compositions may also be calculated for various derivatives of the benzene and xylene produced according to the invention. The results are shown in Table 1.

TABLE 1

| Component | $\delta(^{13}C)$ | | δ(Deuterium) | |
| --- | --- | --- | --- | --- |
| | Low | High | Low | High |
| Ethylbenzene | −60 | −22 | −450 | −213 |
| Cumene | −60 | −21 | −450 | −175 |
| Styrene | −60 | −22 | −450 | −213 |
| Polystyrene | −60 | −22 | −450 | −213 |
| Polyethylene Terephthalate | −57 | −22 | −400 | −175 |
| Phenol | −59 | −24 | −433 | −225 |
| Cyclohexane | −59 | −24 | −450 | −175 |
| Nylon6,6 | −52 | −19 | −400 | −138 |
| Toluene | −59 | −24 | −450 | −250 |

It is to be understood the entirety of ranges shown in Table 1 are included in the scope of this invention that is the polystyrene having any combination of a $\delta(^{13}C)$ value of about −60, −59, −58, −57, −56, −55, −54, −53, −52, −51, −50, −49, −48, −47, −46, −45, −44, −42, −40, −38, −36, −34, −32, −30, −28, −26, −24, or −22; and a δ(deuterium) value of about −450, −440, −430, −420, −410, −400, −390, −380, −370, −360, −350, −340, −330, −320, −310, −300, −290, −280, −270, −260, −250, −240, −230, −220, or −213.

It is to be understood the entirety of ranges shown in Table 1 are included in the scope of this invention that is the polyethylene terephthalate having any combination of a $\delta(^{13}C)$ value of about −52, −51, −50, −49, −48, −47, −46, −45, −44, −42, −40, −38, −36, −34, −32, −30, −28, −26, −24, −22, −20, or, −19; and a δ(deuterium) value of about −400, −390, −380, −370, −360, −350, −340, −330, −320, −310, −300, −290, −280, −270, −260, −250, −240, −230, −220, or −210, −200, −190, −180, or −175.

It is to be understood the entirety of ranges shown in Table 1 are included in the scope of this invention that is the nylon having any combination of a $\delta(^{13}C)$ value of about −57, −56, −55, −54, −53, −52, −51, −50, −49, −48, −47, −46, −45, −44, −42, −40, −38, −36, −34, −32, −30, −28, −26, −24, or −22; and a δ(deuterium) value of about −400, −390, −380, −370, −360, −350, −340, −330, −320, −310, −300, −290, −280, −270, −260, −250, −240, −230, −220, or −210, −200, −190, −180, −170, −160, −150, −140, or −138.

In another embodiment, the measured isotope distribution of an aromatic hydrocarbon may be used to identify the type of manufacturing process that was used in its production. Thus, for example, a sample of benzene of unknown origin with a measured δ(deuterium) value of less than −250 and a $\delta(^{13}C)$ value of less than −32 could be uniquely identified as originating from a methane dehydroaromatization process as opposed to a naphtha reforming process. This novel ability to identify the production process of an aromatic hydrocarbon is based on the realization that the amounts of deuterium and $^{13}C$ present in an aromatic hydrocarbon product can serve to differentiate between an aromatic hydrocarbon produced from naphtha, the same aromatic hydrocarbon produced by dehydroaromatization of naturally-occurring geologic methane alone and the same aromatic hydrocarbon produced by dehydroaromatization of naturally-occurring geologic methane and methane produced from $CO_2$.

Furthermore more detailed analytical techniques may be utilized to determine molecular locations of $^{13}C$ and deuterium i.e., as part of the ring structure or as part of a alkyl side branch. The analysis of isotope location may be further utilized to differentiate the products of the current invention.

Additional discussion of isotope distribution can be found in U.S. Pat. No. 7,754,930.

In addition, the present invention can result in LNG enriched in $^{13}$C and deuterium when compared with the LNG that would be produced from a given gas reservoir utilizing conventional gas liquefaction; that is to say gas liquefaction that is not integrated with the process of methane dehydroaromatization to produce aromatics. This result is due to a recognition by the inventors that—during the dehydroaromatization reaction—methane molecules that contain $^{13}$C and/or deuterium are less reactive than those methane molecules that are composed entirely of $^{12}$C and $^{1}$H; therefore—for a partial conversion process configuration—the lighter isotopes will preferentially be converted to aromatic products and heavier isotopes will preferential remain as methane and end up in the LNG product.

Figure 4:
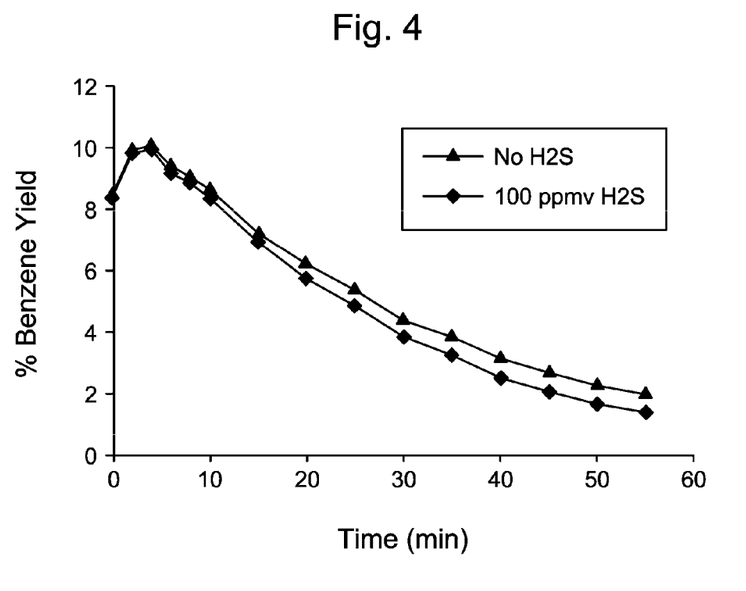
FIG. 4 is a graph of benzene yield against time on stream in the dehydroaromatization process of Example 1 using a methane feed with and without the addition of 100 ppm by volume of $H_2S$.
Figure 5:
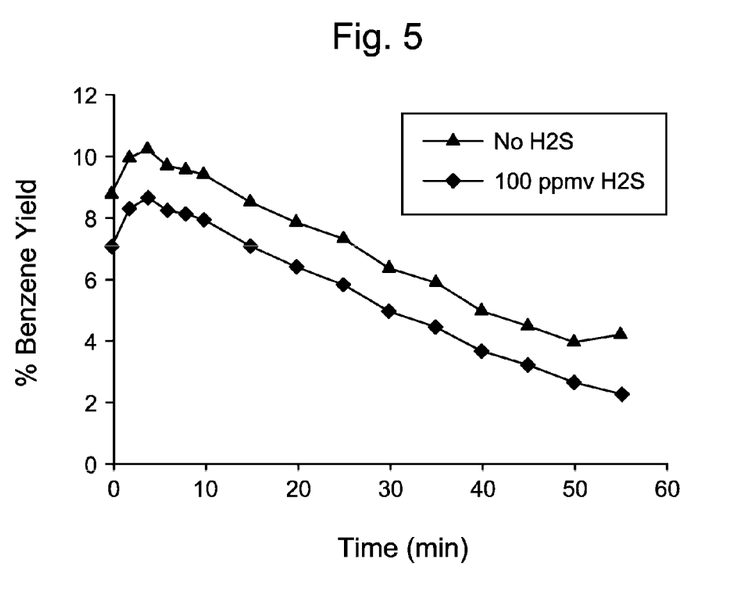
FIG. 5 is a graph of benzene yield against time on stream in the dehydroaromatization process of Example 2 using a methane feed with and without the addition of 100 ppm by volume of $H_2S$.

The invention will now be more particularly described with reference to the following non-limiting Examples and FIGS. 4 and 5 of the accompanying drawings.

Example 1

A 2.7 wt % Mo/ZSM-5 catalyst was prepared by blending ZSM-5 having a silica to alumina molar ratio of 25:1 with MoO$_3$ and then calcining the resultant blend at 500° C. in air for 5 hours.

The catalyst was then heated to 800° C. in helium, after which the helium was replaced by a 95% methane/5% argon feed supplied at a rate sufficient to give a WHSV of 4 hr$^{-1}$. The benzene yield was measured over a period of 60 minutes on stream and the results are shown in FIG. 4.

The above experiment was repeated but with the 95% methane/5% argon feed containing 100 ppm by volume of H$_2$S. Again the benzene yield was measured over a period of 60 minutes on stream and the results are shown in FIG. 4. Surprisingly, it was found that the presence of 100 ppm by volume of H$_2$S had no significant impact on the benzene yield.

Example 2

The procedure of Example 1 was repeated but with the 2.7 wt % Mo/ZSM-5 catalyst being subjected to precarburization by heating in a mixture of 15% CH$_4$/85% H$_2$ to 650° C. before being heated to 800° C. in helium. In one test the precarburization mixture also contained 100 ppm by volume of H$_2$S, while in another test the precarburization mixture contained only CH$_4$ and H$_2$. The results are shown in FIG. 5 and show that the benzene yield was slightly reduced when the MoO$_3$ precarburization was conducted in the presence of H$_2$S.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for converting a gaseous hydrocarbon feed comprising methane to an aromatic hydrocarbon and liquefied natural gas (LNG) and/or pipeline gas, the process comprising:
   (a) supplying said gaseous hydrocarbon feed to a conversion zone comprising at least one dehydroaromatization catalyst;
   (b) contacting said gaseous hydrocarbon feed in said conversion zone with said at least one dehydroaromatization catalyst under conversion conditions to produce a gaseous effluent stream comprising at least one aromatic compound, unreacted methane and H$_2$;
   (c) separating said gaseous effluent stream into a first product stream comprising said at least one aromatic compound and a second product stream comprising unreacted methane and H$_2$;
   (d) separating said second product stream into a methane-rich stream and a hydrogen-rich stream; and
   (e) passing at least part of the methane-rich stream to LNG and/or pipeline gas production, wherein said gaseous hydrocarbon feed supplied to said conversion zone in (a) has a sulfur level of at least 200 ppm by volume.

2. The process of claim 1, wherein said gaseous hydrocarbon feed supplied to said conversion zone in (a) has a CO$_2$ level greater than 50 ppm by volume, up to about 10% by volume.

3. The process of claim 1, wherein said gaseous hydrocarbon feed supplied to said conversion zone in (a) has a dew point between about 203° K and an upper water concentration of about 10% by volume.

4. The process of claim 1, wherein said gaseous hydrocarbon feed supplied to said conversion zone in (a) has a nitrogen content between about 0.1% by volume and about 50% by volume.

5. The process of claim 1, wherein said gaseous hydrocarbon feedstream supplied to said conversion zone in (a) contains between about 0.5% by volume and about 10% by volume of ethane.

6. The process of claim 1, further comprising:
   (f) separating a natural gas stream into a first fraction rich in methane and a second fraction rich in ethane;
   (g) heating first fraction in a first furnace to produce said gaseous hydrocarbon feed comprising methane;
   (h) separately heating said second fraction in a second furnace; and
   (i) supplying said heated second fraction, together with said gaseous hydrocarbon feed comprising methane, to said conversion zone.

7. The process of claim 1, wherein separation (d) is effected by cryogenic separation to produce a liquid methane-rich stream.

8. The process of claim 1, further including removing at least one impurity selected from CO, CO$_2$, H$_2$S, and olefins from said second product stream.

9. The process of claim 8, wherein said olefins are removed from said second product stream by cryogenic separation.

10. The process of claim 8, wherein said olefins are removed from said second product stream by hydrogenation.

11. The process of claim 1, further including removing at least one impurity selected from CO, O$_2$ and N$_2$ from said second product stream in said separation (d).

12. The process of claim 1, wherein at least part of said hydrogen-rich stream is employed to regenerate said at least one dehydroaromatization catalyst.

13. The process of claim 1, wherein at least part of said hydrogen-rich stream is reacted with CO$_2$ and/or CO to produce methanol.

14. The process of claim 13, wherein at least part of said methanol is reacted with benzene produced in said contacting (b) to produce xylene.

15. The process of claim 13, wherein the pressure of said gaseous effluent stream exiting the conversion zone is at a pressure of at least 40 psia (275 kPa).

16. The process of claim 13, wherein the pressure of said gaseous effluent stream exiting the conversion zone is at a pressure of at least 100 psia (690 kPa).

17. A process for converting a natural gas stream to an aromatic hydrocarbon and liquefied natural gas (LNG) and/or pipeline gas, the process comprising:
  (a) treating said natural gas stream to reduce the levels of sulfur, carbon dioxide and water therein and produce a gaseous hydrocarbon feed comprising methane, at least 200 ppm by volume of sulfur and greater than 50 ppm by volume of $CO_2$ and having a dew point of at least 203° K;
  (b) supplying said gaseous hydrocarbon feed to a conversion zone comprising at least one dehydroaromatization catalyst;
  (c) contacting said gaseous hydrocarbon feed in said conversion zone with said at least one dehydroaromatization catalyst under conversion conditions to produce a gaseous effluent stream comprising at least one aromatic compound, unreacted methane and $H_2$;
  (d) separating said gaseous effluent stream into a first product stream comprising said at least one aromatic compound and a second product stream comprising unreacted methane and $H_2$;
  (e) separating said second product stream into a methane-rich stream and a hydrogen-rich stream;
  (f) treating said methane-rich stream to reduce $H_2S$ in said stream; and
  (g) passing at least part of said methane-rich stream to LNG and/or pipeline gas production.

18. The process of claim 17, wherein said sulfur level of said gaseous hydrocarbon feed is controlled by an upstream feed sulfur removal process.

\* \* \* \* \*